(12) United States Patent
Lemmens et al.

(10) Patent No.: US 6,830,933 B2
(45) Date of Patent: Dec. 14, 2004

(54) REFERENCE STANDARDS FOR DETERMINING THE PURITY OR STABILITY OF AMLODIPINE MALEATE AND PROCESSES THEREFOR

(75) Inventors: Jacobus M Lemmens, Mook (NL); Theodorus H. A. Peters, Arnhem (NL); Peter F. A. Bakker, Veghel (NL); Frantisek Picha, Brno (CZ)

(73) Assignee: Synthon BV, Nijmegen (NL)

( * ) Notice: Subject to any disclaimer, the term of this patent is extended or adjusted under 35 U.S.C. 154(b) by 473 days.

(21) Appl. No.: 09/938,819

(22) Filed: Aug. 27, 2001

(65) Prior Publication Data

US 2002/0137223 A1 Sep. 26, 2002

Related U.S. Application Data

(63) Continuation of application No. 09/809,347, filed on Mar. 16, 2001, now abandoned.
(60) Provisional application No. 60/258,601, filed on Dec. 29, 2000.

(51) Int. Cl.[7] .............................................. G01N 33/00
(52) U.S. Cl. ..................... 436/96; 436/161; 436/162; 436/175; 436/177; 422/70
(58) Field of Search ............................. 436/8, 96, 161, 436/162, 174, 175, 177, 183; 422/68.1, 70; 210/656, 658, 198.2, 198.3

(56) References Cited

U.S. PATENT DOCUMENTS

| | | |
|---|---|---|
| 4,572,909 A | 2/1986 | Campbell et al. |
| 4,879,303 A | 11/1989 | Davison et al. |
| 4,983,740 A | 1/1991 | Peglion et al. |
| 5,155,120 A | 10/1992 | Lazar et al. |
| 5,389,654 A | 2/1995 | Furlan et al. |
| 5,438,145 A | 8/1995 | Furlan et al. |
| 6,046,337 A | 4/2000 | Bozsing et al. |

FOREIGN PATENT DOCUMENTS

| | | |
|---|---|---|
| EP | 0 089 167 B1 | 10/1986 |
| EP | 0 244 944 | 1/1990 |
| EP | 0 290 211 B1 | 9/1991 |
| EP | 0 534 520 B1 | 3/1997 |
| EP | 0 902 016 A1 | 3/1999 |
| EP | 0 963 980 A2 | 12/1999 |
| WO | 99/25688 | 5/1999 |
| WO | 99/52873 | 10/1999 |
| WO | 00/24714 | 5/2000 |
| WO | 00/35873 | 6/2000 |
| WO | 00/35910 | 6/2000 |

OTHER PUBLICATIONS

Alker et al., "Long–acting dihydropyridine calcium antagonists. 9. Structure activity relationships around amlodipine", Eur J Med Chem (1991) 26, 907–913.
Amlodipine Besylate Monograph, PHARMEUROPA vol. 10, No. 2, 197–198, Jun. 1998.
Faulkner et al, "Absorption of Amlodipine Unaffected by Food", Arzneim Forsch/Drug Res. 39 (11), No. 7, (1989).
McDaid and Deasy, "Formulation development of a transdermal drug delivery system for amlodipine base", International Journal of Pharmaceutics 133 (1996) 71–83.
Arrowsmith et al., "Long–Acting Dihydropyridine Calcium Antagonists. 1. 2–Alkoxymethyl Derivatives Incorporating Basic Substituents", J. Med. Chem. American Chemical Society, 1986, 29, 1696–1702.
FDA FOIA Material on Amlopidine Besylate, NDA No. 19–787, "Review of an Original NDA", Oct. 10, 1990.

*Primary Examiner*—Maureen M. Wallenhorst
(74) *Attorney, Agent, or Firm*—Mark R. Buscher (57) ABSTRACT

Amlodipine aspartate and amlodipine maleamide are used as reference standards or markers in determining the purity of amlodipine maleate substances and products.

16 Claims, 7 Drawing Sheets

REFERENCE STANDARDS FOR DETERMINING THE PURITY OR STABILITY OF AMLODIPINE MALEATE AND PROCESSES THEREFOR

This application is a continuing application under 35 U.S.C. §120 from prior U.S. patent application Ser. No. 09/809,347, filed Mar. 16, 2001, now abandoned, the entire contents of which are incorporated herein by reference. Further, this application claims the benefit of priority under 35 U.S.C. §119(e) from provisional application Serial No. 60/258,601, filed Dec. 29, 2000, the entire contents of which are incorporated herein by reference.

BACKGROUND OF THE INVENTION

1. Field of the Invention

The present invention relates to the use of two novel compounds as reference standards for determining the purity or stability of amlodipine maleate substances and pharmaceutical compositions.

2. Description of the Related Arts

Pharmaceutical products are regulated in most countries by a government agency. For example, the U.S. Food & Drug Administration (FDA) generally requires an applicant to show safety and efficacy of the pharmaceutical product during the approval/review phase and continues to monitor the safety of the drug post-approval. Similar requirements exist in many European countries and elsewhere in the world. In order to satisfy safety concerns, the regulatory agencies generally require a manufacturing specification that sets the maximum amount of each identified impurity as well as the maximum amount for all remaining unidentified impurities. Once approved, each batch or lot of the pharmaceutical product is tested to insure that the specification is met. Further, stability testing is performed on the pharmaceutical product in order to show that the composition does not substantially or materially change over time; i.e. over its indicated shelf-life. It is important that before its administration to a patient that the pharmaceutical product does not deviate from its approved specification in a way that might detract from its safety or efficacy. Good practice warrants keeping a sample from every commercial batch released to the public so that the stability can be monitored and any defect uncovered and corrected.

Accordingly, pharmaceuticals are tested for purity both during manufacture and subsequently during its shelf-life. Typically, the product is tested by comparing certain analytical results with those of a standard reference result. For impurity detection, this normally means assaying the pharmaceutical product and comparing the result to the result obtained for a substantially pure form of the suspected impurity in the same assay. Sources of potential impurities in a pharmaceutically active agent or formulation include:

residual amounts of synthetic precursors side product arisen from the synthesis and elaboration of the active substance residual solvents degradation products appearing during storage including products resulted form interactions with excipients in formulations isomers of the active agent trace contaminants e.g. from equipment and environment.

Without identification of the potential impurity and a synthetic route to make a reference standard therefore, it is difficult or impossible to efficiently assay for the impurity or to otherwise monitor its level in the pharmaceutical product.

Amlodipine besylate is a highly successful pharmaceutical sold by Pfizer under the tradename NORVASC for treating hypertension and angina. Amlodipine itself was first patented in EP 089 167 and corresponding U.S. Pat. No. 4,572,909. These patents identify that one of the most preferred compounds is 2-[(2-aminoethoxy)methyl]-4-(2-chlorophenyl)-3-ethoxycarbonyl-5-methoxycarbonyl-6-methyl-1,4-dihydropyridine. This compound, which is now commonly known as amlodipine, has the following formula:

Examples 8, 11, 12, and 22 of EP 089 167 show the synthesis of amlodipine in the maleate salt form. While a variety of acid addition salts are generically taught to be suitable, the maleate salt is identified as the most preferred acid addition salt. However, subsequently EP 244 944 and corresponding U.S. Pat. No. 4,879,303 were issued directed to the besylate (or benzene sulfonate) salt of amlodipine. The besylate salt is stated to provide certain advantages over the known salts including good formulating properties. The quality standards for amlodipine besylate is provided in Pharmeuropa 10(2),187 (1998).

Indeed, a review of the available portions of the NORVASC (amlodipine besylate) New Drug Application (NDA) filed with the U.S. Food & Drug Administration by Pfizer reveals that a switch was made during development from the original maleate salt to the later besylate salt. (See "Review of Original NDA" for NDA# 19-787 of 10.10.1990, obtainable from FDA under Freedom of Information Act). The reasons for the switch were apparently tableting and stability problems. However, the precise stability and tableting problems/issues/causes are not publicly disclosed in the information available from the FDA.

Amlodipine maleate is, however, still a useful salt of amlodipine. It would be desirable to identify and solve the stability problems associated therewith and to provide a method for monitoring its production.

SUMMARY OF THE INVENTION

The present invention relates to the discovery of two novel impurities associated with amlodipine maleate substances and its pharmaceutical compositions. One aspect of the present invention relates to a process which comprises assaying a substantially pure amlodipine aspartate or amlodipine maleamide under a set of conditions to obtain a reference standard analytical result for said set of conditions. A further aspect of the invention relates to a process of testing purity or stability of a sample of amlodipine maleate or a pharmaceutical dosage form comprising amlodipine maleate which comprises assaying a sample of an amlodipine maleate substance or composition for the presence of amlodipine aspartate or amlodipine maleamide. For example, a process for checking the purity or stability of an amlodipine maleate substance or composition that comprises assaying an amlodipine maleate substance or composition to obtain an analytical result; and comparing the analytical result to a corresponding reference standard analytical result for amlodipine aspartate or amlodipine maleamide to determine if the purity or stability of the amlodipine maleate substance or composition is satisfactory. Another aspect of the invention relates to a process for producing pharmaceutically suitable amlodipine maleate solid dosage forms. The process comprises blending amlodipine maleate with at least one pharmaceutically acceptable excipient to form a blend; either (a) filling the blend into capsules or (b) compressing the blend in to tablets, to form a production lot of amlodipine maleate pharmaceutical solid dosage forms; removing a sample of said amlodipine maleate pharmaceutical solid dosage forms from the production lot; subjecting the sample to an assay to obtain a sample analytical result; comparing the sample analytical result to a corresponding reference standard analytical result for amlodipine aspartate or amlodipine maleamide to determine the amount of amlodipine aspartate or amlodipine maleamide relative to said amlodipine maleate; and selling or releasing the production lot if the relative amount of amlodipine aspartate or amlodipine maleamide is not greater than the pre-determined/approved limit, e.g. 1.0 wt %, preferably 0.1 wt % based on the amount of amlodipine maleate.

DETAILED DESCRIPTION OF THE INVENTION

Amlodipine maleate has the following formula:

It has now been found that at least two heretofore unidentified impurities should be taken into consideration in testing the quality of amlodipine maleate. Both are contaminants arising from side reactions during the synthesis and/or formed during storage. The contaminants are specific to amlodipine maleate as they arise from the presence of maleic acid and thus are not identified or monitored in connection with amlodipine besylate. The compounds are referred to herein as amlodipine aspartate and amlodipine maleamide. The formula for each is given below.

"Amlodipine Aspartate"

"Amlodipine Maleamide"

Both amlodipine aspartate and amlodipine maleamide are themselves calcium channel blockers and can be used as pharmaceutical active agents. These novel compounds and their use in pharmaceuticals is more fully described in described in commonly-owned co-pending U.S. patent application Ser. No. 09/809,349, filed on Mar. 16, 2001, and entitled "Aspartate Derivative of Amlodipine," the entire contents of which are incorporated herein by reference, and in commonly-owned co-pending U.S. patent application Ser. No. 09/809,348, filed on Mar. 16, 2001, and entitled "Amide derivative of Amlodipine," the entire contents of which are incorporated herein by reference.

These compounds are formed by a reaction between amlodipine and maleic acid. Amlodipine aspartate is formed by a Michael addition between the amino group of amlodipine and the double bond of the maleic acid. Amlodipine maleamide is formed by an amidation reaction of the amine group of the amlodipine with the carboxyl group of the maleic acid.

Chemical reactions between amlodipine and maleic acid leading to the aspartate and maleamide impurities can occur as a side product during the formation of the amlodipine maleate salt. Further, the amlodipine maleate can undergo subsequent conversion/degradation by the above-mentioned Michael addition or amidation reactions to form the aspartate or maleamide impurity, respectively, during handling and formulating into a pharmaceutical final form or during subsequent storage. As between the two impurities, the amlodipine aspartate is more easily formed, especially during storage conditions, and thus tends to be the more important impurity to monitor. Although these compounds may not be harmful in the pharmaceutical composition, being themselves calcium channel blockers, modern regulatory practice generally requires precise control over such "impurities." Having now identified the impurities and prepared them in a sufficiently pure state, amlodipine aspartate and amlodipine maleamide can be used as reference markers for routine analysis of amlodipine maleate or pharmaceutical dosage forms comprising it, both during development works targeted to solve the above-mentioned stability issues or during industrial production of amlodipine maleate and pharmaceutical forms based thereon.

Synthesizing amlodipine aspartate for use as a reference standard or marker can be achieved by bringing amlodipine free base or a salt thereof and maleic acid into intimate contact with each other under Michael addition conditions. The reaction is illustrated below.

In general, conditions of higher pH, higher temperature, and longer reaction/contact time tend to improve the addition reaction. Preferably the pH of the environment is always above 7, preferably above 7.5. Lower pH's tend to inhibit the addition and prevent the reaction. Further, the reaction is preferably carried out in a melt phase or in a solution. A "melt phase" means that amlodipine is melted at least momentarily while in the presence of maleic acid. When carried out in solution, the temperature is preferably at least 60° C., more preferably at least 80° C., and typically within the range of 85° C. to 110° C. Among solvents suitable for the addition reaction are polar aprotic solvents, for example N,N-dimethylformamide, alcohols such as ethanol and isopropanol, esters such as ethyl acetate, and hydrocarbons such as toluene.

The amlodipine and maleic acid are normally combined in approximately stoichiometric ratios, namely 0.9:1 to 1:0.9. A convenient method to carry out the reaction is to melt amlodipine maleate. While the maleic acid is in effect pre-combined with the amlodipine, such is specifically contemplated as being within the scope of the present invention. Alternatively, amlodipine free base and amlodipine maleate can be combined in a solvent or dry mixed and melted, etc. to carry out the reaction.

Amlodipine maleamide can be synthesized by reacting amlodipine or a salt thereof with a carbonyl-activated maleic acid compound. The reaction is essentially an amidation reaction and thus is favored by the presence of an acid catalyst, elevated temperature, etc., and such other amidation conditions as are well known by workers skilled in the art. A "carbonyl-activated maleic acid compound" means maleic acid or a derivative thereof that has a sufficiently activated carbonyl group to facilitate the amidation reaction with amlodipine. In some embodiments the carbonyl activation is achieved by the presence of an acid catalyst, typically a Lewis acid such as aluminium chloride or phosphoric acid. However, the preferred embodiment is to use maleic acid anhydride which provides an activated carbonyl group without the necessity of a catalyst. Maleic acid per se and in the absence of a catalyst or activator is not a carbonyl-activated maleic acid compound and will not readily form amlodipine maleamide, even if placed in the presence of amlodipine. The reaction with maleic acid anhydride is set forth below.

In general, the reaction can be carried out by bringing amlodipine free base or a salt thereof and the activated-carbonyl maleic acid compound into intimate contact with each other. Preferably, the reaction is carried out at an elevated temperature such as 25–100° C., more typically 35–50° C., and in an appropriate solvent. Among solvents suitable for the addition reaction are polar aprotic solvents, for example N,N-dimethylformamide, alcohols such as ethanol and isopropanol, esters such as ethyl acetate, and hydrocarbons such as toluene. The amlodipine and carbonyl-activated maleic acid compound are normally combined in approximately stoichiometric ratios, namely 0.9:1 to 1:0.9.

Amlodipine aspartate and amlodipine maleamide can each be used as a reference standard (or reference marker) in an assay for determining the presence and/or level of the impurity in a sample of an amlodipine maleate substance or pharmaceutical composition. As a reference standard the amlodipine aspartate or maleamide should be in a suitably pure form, typically at least 80%, more preferably at least 90%. Higher purity levels are attainable, but are not essential. The amlodipine aspartate and amlodipine maleamide produced as described above may be further purified if necessary to achieve the desired purity level. Purification may be carried out by conventional methods; for instance, by recrystallization from a suitable solvent or by stirring, optionally under heating, a suspension of the compound in a suitable liquid with subsequent removal of the liquid phase.

The assay useful in the present invention is not particularly limited and includes any technique that can resolve or otherwise detect the presence of the target compound. In general, assays can be divided into techniques based on physical separation of the target compound(s) from the sample and non-separating or observation-based techniques such as IR and NMR, although other techniques are also possible. Preferably the assay is based on a separation. Examples of this type of assay include thin layer chromatography (TLC) and high performance liquid chromatography (HPLC).

The amlodipine aspartate or amlodipine maleamide is assayed under a set of conditions to produce a reference standard analytical result. A "reference standard analytical result" may be a quantitative or qualitative result and can be in any form including numerical, graphical, pictorial, etc. In some cases the result can be stored electronically for later comparisons.

The amlodipine maleate material to be assayed for the presence of either amlodipine aspartate and amlodipine maleamide comprises amlodipine maleate substances and compositions. The term "amlodipine maleate substance" is used herein to denote a material that contains primarily only amlodipine maleate. Examples of the substance include the crude amlodipine maleate recovered during synthesis as well as purified amlodipine maleate. "Amlodipine maleate compositions" include mixtures, blends, solutions, suspensions, etc. that contain amlodipine maleate. Examples of compositions include the blended, powdery composition used in tabletting techniques to form tablets as well as intermediates therefore and final dosage forms. The compositions may be further processed in order to carry out the assay, i.e. crushing a tablet to obtain a powder, and such modifications are included within the scope of the composition. The amlodipine maleate per se can be of any suitable form including crystalline forms or amorphous forms.

A preferred amlodipine maleate composition to be tested is a pharmaceutical solid dosage form. A pharmaceutical solid dosage form includes tablets, capsules, sachets, etc. that comprise amlodipine maleate, in a pharmaceutically effective amount, and at least one pharmaceutically acceptable excipient such as a binder, filler, diluent, lubricant, disintegrant, etc. Such compositions are made by methods well known in the art including wet granulation, dry granulation and direct compression for tablets and blending and filling for making capsules. In both cases, a blend is formed by blending amlodipine maleate with at least one pharmaceutically acceptable excipient. The blend is then further processed including filling it into capsules or compressing it into tablets as desired. It should be noted that blending or granulating embraces both wet and dry processing methods. Preferred amlodipine maleate pharmaceutical compositions have a pH in the range of 5.5 to 7, measured as a 20 wt % aqueous slurry, and thus exhibits improved stability as is more fully described in commonly-owned co-pending U.S. patent application Ser. No. 09/809,346, filed on Mar. 16, 2001, and entitled "Pharmaceutical Compositions Comprising Amlodipine Maleate," the entire contents of which are incorporated herein by reference.

For quality control purposes, it is preferred that the pharmaceutical composition be made from amlodipine maleate that has a low level of amlodipine aspartate or amlodipine maleamide. A convenient way to make amlodipine and convert it to the maleate salt thereof with a minimum of impurity formation and in good yields is more fully described in commonly owned co-pending U.S. application Ser. No. 09/809,351, filed on Mar. 16, 2001, and entitled "Process for Making Amlodipine, Derivatives Thereof, and Precursors Therefor," the entire contents of which are incorporated herein by reference, and commonly owned co-pending U.S. patent application Ser. No. 09/809, 343, filed on Mar. 16, 2001, and entitled "Process for Making Amlodipine Maleate," the entire contents of which are incorporated herein by reference.

Typically pharmaceutical compositions are made in batches or lots for production purposes. Production lots are typically 100,000 to 1,000,000 or more tablets or capsules. A production lot should be checked to insure that the level of amlodipine aspartate or amlodipine maleamide is within specification; i.e., a quality control test. A sample from the production lot (e.g. 10 to 100 capsules or tablets) is taken and assayed for the presence of amlodipine aspartate or amlodipine maleamide and preferably also for the content of the same. Preferably the amlodipine maleate pharmaceutical compositions contain less than 1%, more preferably less than 0.5%, and most preferably less than 0.2% amlodipine aspartate or amlodipine maleamide based on the amount of amlodipine maleate. Generally the entire production lot, minus any retained sample(s), will be sold or otherwise released by the manufacturer unless an unacceptable level of amlodipine aspartate or amlodipine maleamide is found. In that case, the production lot will not be sold or released; i.e. neither placed in commerce nor used in clinical studies.

The same strategy can be applied for production lots of amlodipine maleate substance. A sample from the production lot (e.g. 0.5–2 g of the material) is taken and assayed for the presence of amlodipine aspartate or amlodipine maleamide and preferably also for the content of the same. Preferably the amlodipine maleate substance contains less than 1%, more preferably less than 0.5%, and most preferably less than 0.1% of amlodipine aspartate or amlodipine maleamide based on the amount of amlodipine maleate. Generally the entire production lot, minus any retained sample(s), will be sold or otherwise released by the manufacturer unless an unacceptable level of amlodipine aspartate or amlodipine maleamide is found. In that case, the production lot will not be sold or released; i.e. neither placed in commerce nor used in production of pharmaceutical products.

Generally the assaying of the amlodipine maleate material results in an analytical result for the sample. Typically the "sample analytical result" is compared in some fashion to the reference standard analytical result for either amlodipine aspartate or amlodipine maleamide. The comparison can be done manually such as by visual observation and/or by an automated procedure. The reference standard analytical result can be obtained essentially concurrently with the sample analytical result such as immediately before, during or immediately after the assaying of the amlodipine maleate sample, or they can be obtained earlier, even months or years earlier. In some embodiments the reference standard analytical result is electronically stored and used by a computer algorithm to determine the presence of the aspartate or maleamide and its amount. This latter embodiment includes calibrating the equipment based on the reference standard analytical results or results derived therefrom and/or providing a so-called internal normalization. All such comparisons, whether direct, indirect, manual or automated, are included within the meaning of "comparing."

The assay used in determining the reference standard analytical results is generally also the same assay with the same set of conditions used to test the amlodipine maleate material, although such is not necessarily required.

The invention will be further described with reference to the two preferred assay techniques, namely TLC and HPLC. In TLC, samples of the tested amlodipine maleate material, and reference standard(s) containing known amounts of amlodipine aspartate and/or amlodipine maleamide are chromatographed on a suitable chromatographic plate by a suitable developing liquid (mobile phase) under set conditions. These conditions include the solvent, the concentration of the amlodipine derivative in the solvent and the amount of solution applied to the plate. Selecting appropriate solvents and concentrations is well known within the art. The analytical results produced under these conditions may include the $R_f$ value, namely the ratio of distance traveled by the corresponding material to the distance traveled by the solvent, and/or the size of the spot produced on the chromatogram.

Preferably, the reference standard is applied at the same time and to the same chromatographic plate as the tested sample thereby allowing for side-by-side comparisons. In other embodiments the reference standard is already defined and is simply compared with the developed sample chromatogram.

Thus one process for testing the purity and/or stability to degradation of a sample comprising amlodipine maleate comprises the steps of:
 a) dissolving a sample comprising amlodipine maleate in a solvent to produce a sample solution
 b) dissolving a sample of amlodipine aspartate and/or amlodipine maleamide in a solvent to produce a reference solution
 c) subjecting the sample solution and the reference solution to thin layer chromatography to obtain a TLC chromatogram for each and
 d) estimating the intensity of any secondary spot obtained from the sample solution which corresponds in $R_f$ value to the reference marker, against the intensity of the spot due to the aspartate or maleamide in the chromatogram of the reference solution. It should be noted that the reference solution can be a "mixed" reference solution in that it can contain both the aspartate and another reference material of known purity, i.e., further containing a known amount and purity of amlodipine and/or amlodipine maleamide, etc.

Similarly an assay using HPLC can also be formulated. The reference standard analytical results may include the resolution factor, response factor, the retention time, and/or the peak area for the aspartate or maleamide. For example, a process for testing the purity and/or stability to degradation of a sample comprising amlodipine maleate comprises the steps of:
 a) dissolving a sample comprising amlodipine maleate in a solvent to produce one or more sample solutions
 b) dissolving a sample of amlodipine aspartate or amlodipine maleamide in a solvent to produce a reference solution
 c) injecting the sample and reference solutions into an HPLC column and
 d) estimating the peak areas of each solution and calculating from these the content of the amlodipine aspartate and/or amlodipine maleamide in each sample solution.

In this embodiment, it may be necessary or desirable to run a system suitability solution through the HPLC column prior to step c) in order to determine the resolution factor between amlodipine maleate and any other compound present in the sample. In that case the method includes the additional step of
 b') dissolving amlodipine maleate and a suitable external standard(s) to produce a system suitability solution, and injecting the system suitability solution onto the HPLC column to determine resolution factor(s). This is useful to check that the column is still performing within specifications. The suitability solution can be the aspartate or maleamide, but it is not limited thereto and can be any material that shows whether the column still works as designed.

Figure 1:
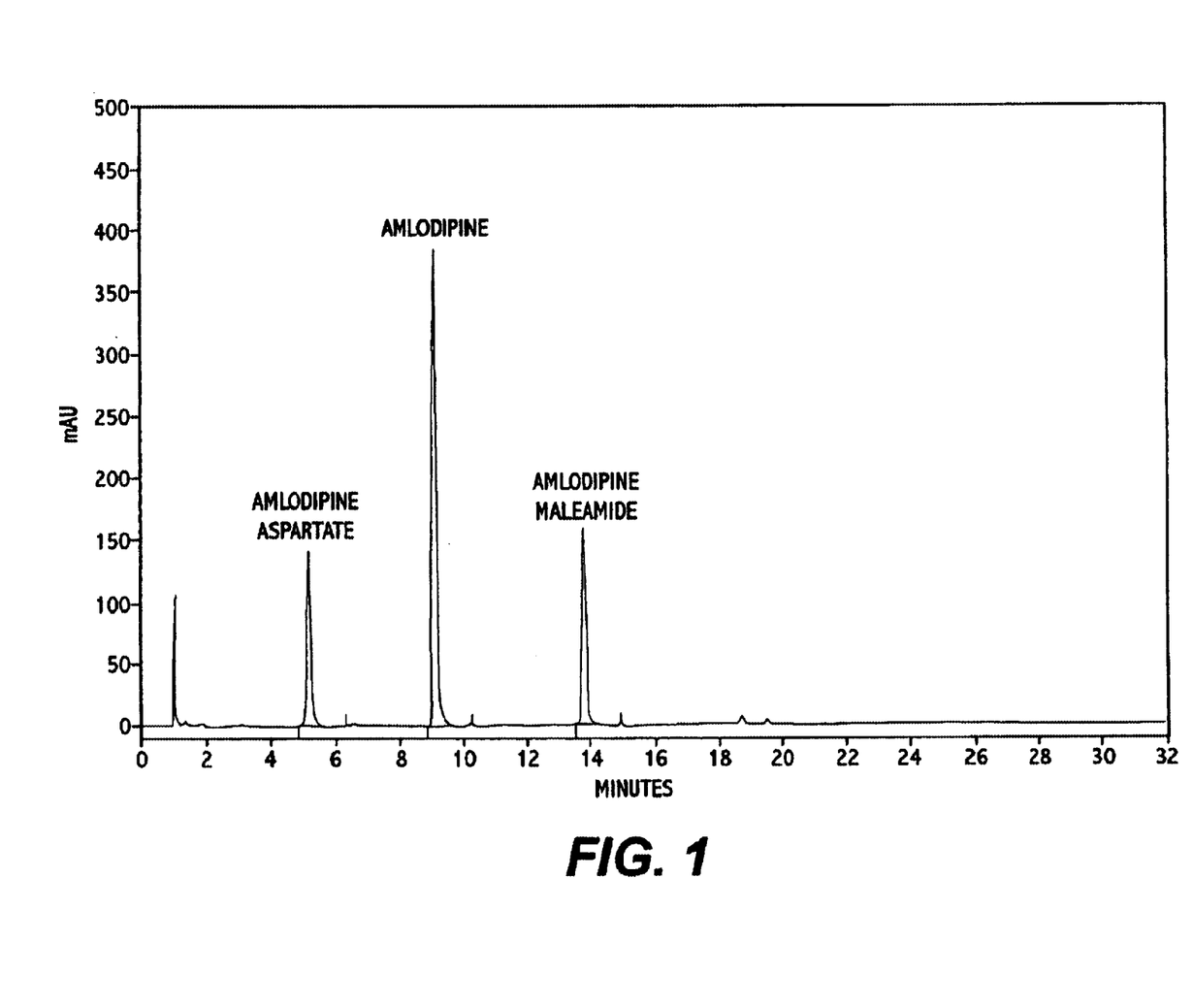
FIG. 1 shows an HPLC chromatogram of an artifical mixture of amlodipine maleate, amlodipine aspartate, and amlodipine maleamide.

FIG. 1 demonstrates that HPLC can be used to resolve amlodipine aspartate and amlodipine maleamide from amlodipine. An artificial mixture of amlodipine, amlodipine aspartate and amlodipine maleamide was subjected to HPLC. The results are shown as an HPLC chromatogram as FIG. 1. Note that peaks corresponding to the aspartate and the maleamide are visible.

As an alternative to assaying a sample of the reference marker separately each time, a parameter known as the Response factor (R) may be used. The response factor is a previously determined ratio of a numerical result (e.g. peak area at HPLC) obtained by testing a sample of the aspartate or the maleamide, by a given analytical technique, to the corresponding numerical result obtained by testing the same amount of pure amlodipine maleate at an equivalent concentration. The known response factor for amlodipine aspartate or amlodipine maleamide can be used to calculate the amount of that particular marker in the test sample. In this way, the relative amount of the impurity to the amlodipine maleate in the sample can be determined as is well known in the art.

In the above embodiments, the need for the solvent to dissolve the amlodipine maleate sample should be understood to require only dissolution of the amlodipine maleate substance and the impurities of interest. Other components such as inert fillers in a pharmaceutical composition need not be soluble in the solvent system and need not be "dissolved" in order to meet the above "dissolving" step, as is conventional in the art for assaying a pharmaceutical dosage form.

The invention also provides the use of a compound selected from amlodipine aspartate (1) or amlodipine maleamide (2) as a reference marker in analyzing the purity or stability against degradation of a batch sample of amlodipine maleate or a batch sample of a pharmaceutical dosage form comprising amlodipine maleate. Such analytical testing of the drug substance or the drug form comprising amlodipine maleate serves principally to confirm that compounds (1) or (2) are absent (i.e. below the detection limit of the analytical method) or are only present at levels below the maximum allowed limit characterizing the pharmaceutical quality of products comprising amlodipine maleate, i.e. a quality allowing the products to be released or sold as pharmaceuticals.

The invention is further described by the following non-limiting examples.

EXAMPLE 1

Process for Making Amlodipine Aspartate 16 g of amlodipine and 12 g of amlodipine maleate were melted in a 300 ml flask. The melted substance was cooled to room temperature and dissolved in 300 ml of dichloromethane. The mixture was extracted with 300 ml of a 1M NaOH solution. The organic layer was discarded and the aqueous layer acidified with 55 ml of a 6 M HCl solution. The mixture was extracted with 300 ml of dichloromethane. The layers were separated and the organic layer dried over $Na_2SO_4$. The mixture was evaporated to dryness and the remaining solid recrystallised from ethanol. The obtained solid was dried in a vacuum oven at 40° C. leaving 4.7 g of an off white product.

Yield: 4.7 g (39%)
Mp: 178° C.–183° C. (decomposed)
Purity: greater than 90%
$^1$H-NMR spectrum:

The $^1$H-NMR spectrum was measured at 303.2 K on a Bruker Avance-400 in deuterated dimethylsulfoxide at 400 MHz. It is represented on FIG. 2.

Figure 2:
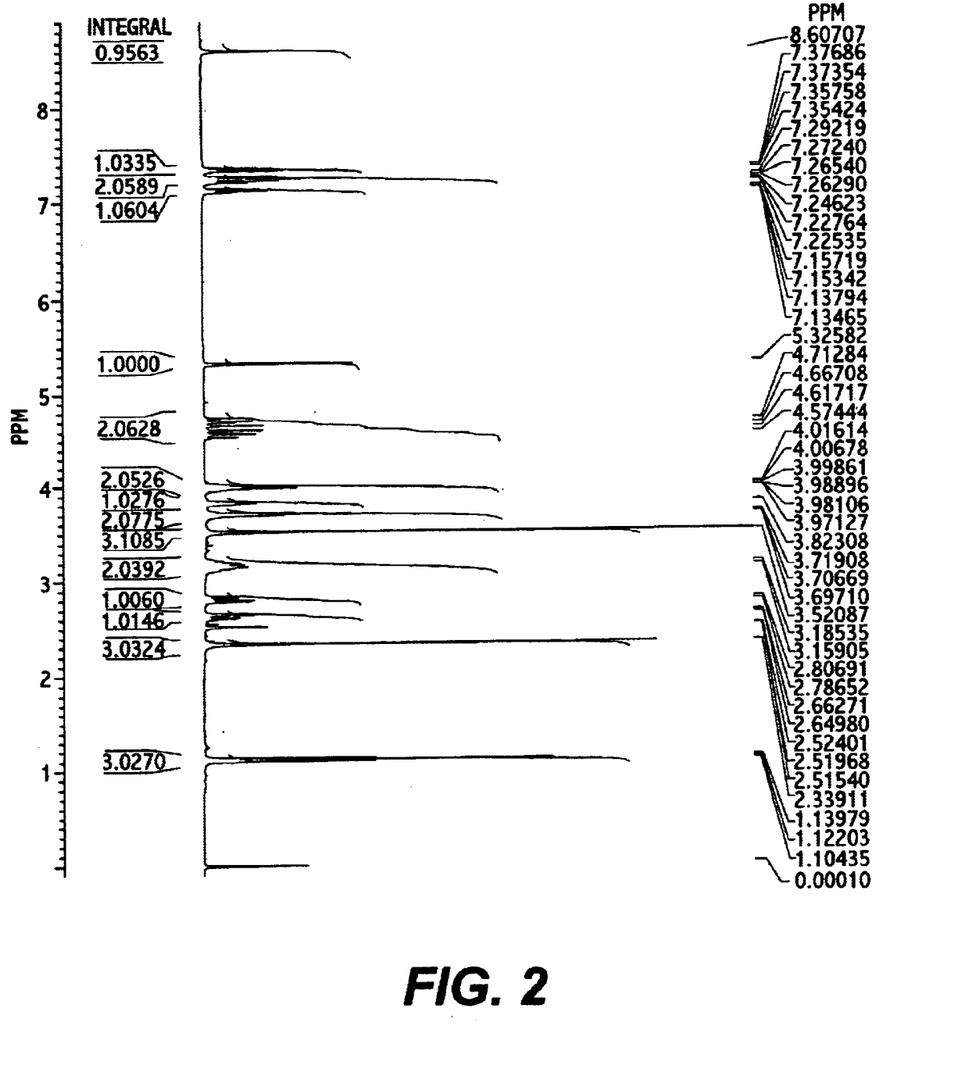
FIG. 2 shows an $^1$H-NMR spectrum of the amlodipine aspartate compound produced in Example 1.

| δ | assignment |
|---|---|
| 1.12 | (t, 3H, $J_{11,12}$ = 7.0 Hz, 3xH-12); |
| 2.36 | (s, 3H, 3xH-15); |
| 2.87 | (m, ~2H, 2xH-3"); |
| 3.24 | (m, ~2H, 2xH-9); |
| 3.52 | (s, ~3H, 3xH-14); |
| 3.76 | (bs, 2H, 2xH-8); |
| 4.00 | (m, 3H, 2xH-11 + H-2"); |
| 4.65 | (m, 2H, 2xH-7); |
| 5.33 | (s, 1H, H-4); |
| 7.13 | (dt, 1H, $J_{3',4'}$ = $J_{4',5'}$ = 7.6 Hz, $J_{4',6'}$ = 1.8 Hz, H-4'); |
| 7.26 | (m, 2H, H-3' + H-5'); |
| 7.37 | (d, 1H, $J_{5',6'}$ = 7.8 Hz, H-6'); |
| 8.61 | (s, 1H, NH). |

$^{13}$C-NMR Spectrum:
The $^{13}$C-NMR spectrum was measured at 303.2 K on a Bruker Avance-400 in deuterated dimethylsulfoxide at 100.6 MHz. It is represented on FIG. 3.

Figure 3:
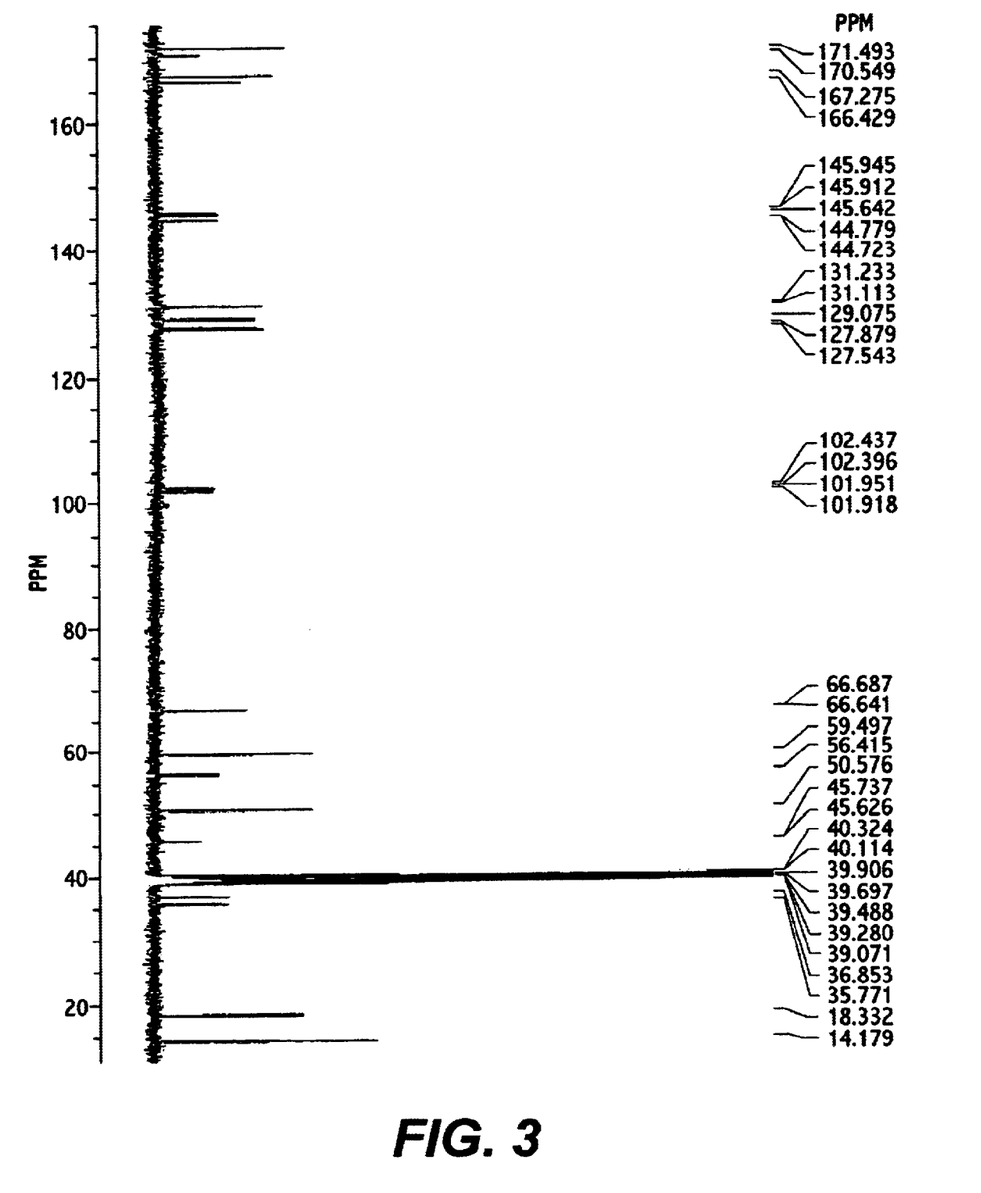
FIG. 3 shows an $^{13}$C-NMR spectrum of the amlodipine aspartate compound produced in Example 1.

| δ | assignment |
|---|---|
| 14.18 | (C-12); |
| 18.33 | (C-15); |
| 35.77 | (C-3"); |
| 36.85 | (C-4); |
| 45.63, 45.74 | (C-9); |
| 50.58 | (C-14); |
| 56.42 | (C-2"); |
| 59.50 | (C-11); |
| 66.64, 66.69 | (C-7, C-8); |
| 101.92, 102.40 | (C-3, C-5); |
| 127.54 | (C-5'); |
| 127.88 | (C-4'); |
| 129.07 | (C-2'); |
| 131.11 | (C-6'); |
| 166.43 | (C-10); |
| 167.28 | (C-13); |
| 170.55, 171.49 | (C-1", C-4"). |

EXAMPLE 2

Preparation of Amlodipine Maleamide 5 g of amlodipine was dissolved in 50 ml of ethyl acetate and heated to 60° C. To this mixture was added 1.15 g of maleic anhydride and the mixture was shaken until the solution was clear. The mixture was cooled to room temperature and left overnight. The mixture was evaporated to dryness and subsequently dried in a high vacuum oven at 25° C. for 3 hours leaving a yellow solid.

Yield: 6.1 g (99%)

Mp: 83° C.–86° C.

Purity: greater than 95% (HPLC)

Figure 4:
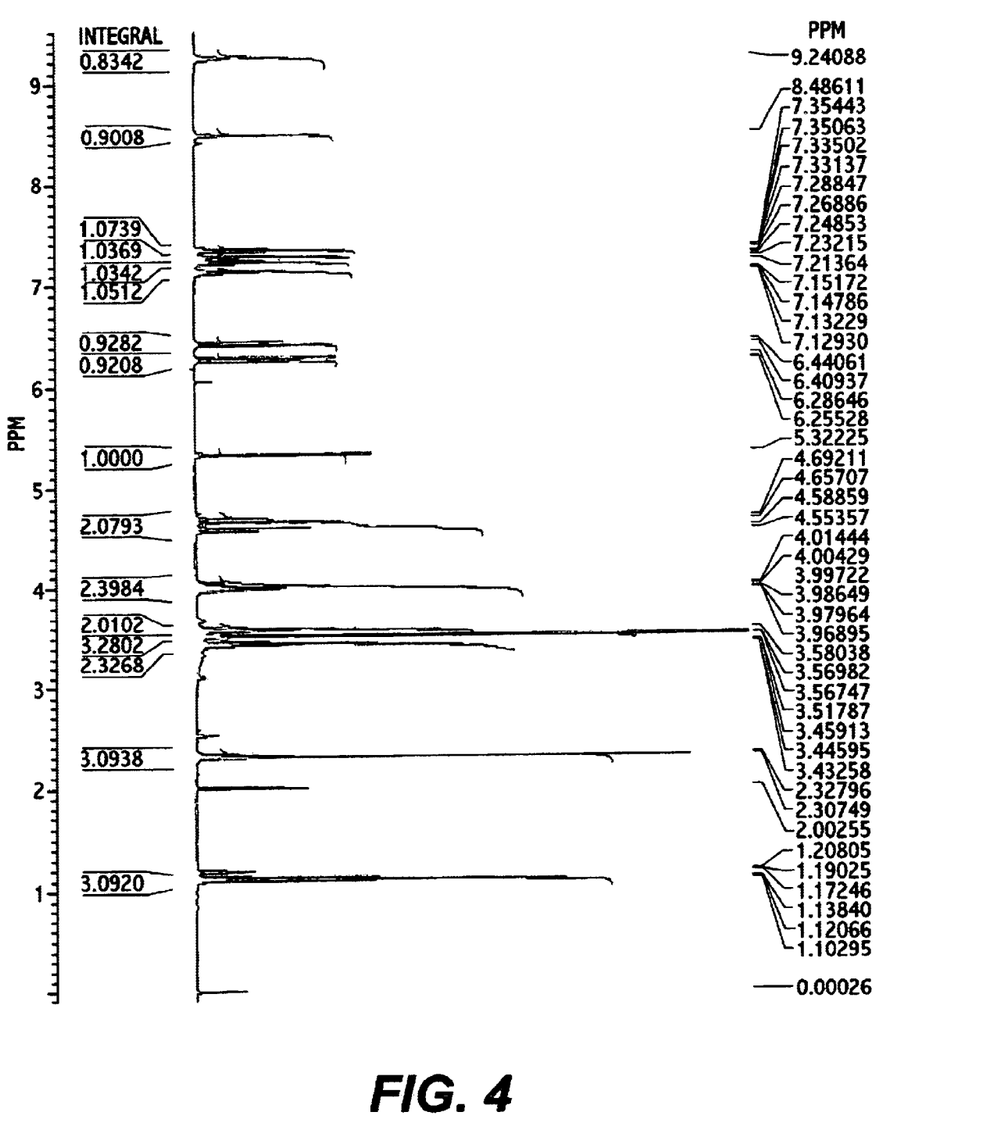
FIG. 4 shows an $^1$H-NMR spectrum of the amlodipine maleamide compound produced in Example 2.

$^1$H-NMR Spectrum:

The $^1$H-NMR spectrum was measured at 303 K on a Bruker Avance-400 in deuterated dimethylsulfoxide at 400 MHz. The spectrum is shown in FIG. 4.

| δ | assignment |
|---|---|
| 1.12 | (t, 3H, $J_{11,12}$ = 7.0 Hz, 12-H3) |
| 2.31 | (s, 3H, 15-H$_3$) |
| 3.44 | (bq, ~2H, 9-H$_2$) |
| 3.52 | (s, ~3H, 14-H$_3$) |
| 3.58 | (bt, 2H, 8-H$_2$) |
| 3.99 | (m, ~2H, 11-H$_2$) |
| 4.62 | (AB q, 2H, 7-H$_2$) |
| 5.32 | (s, 1H, 4-H) |
| 6.27 | (d, ~1H, $J_{4",5"}$ = 12.4 Hz, 4"-H) |
| 6.43 | (d, ~1H, $J_{4",5"}$ = 12.4 Hz, 5"-H) |
| 7.13 | (dt, 1H, $J_{3',4'}$ = $J_{4',5'}$ = 7.7 Hz, $J_{4',6'}$ = 1.6 Hz, 4'-H) |
| 7.23 | (dt, 1H, $J_{4',5'}$ = $J_{5',6'}$ = 7.7 Hz, $J_{3',5'}$ = 1.0 Hz, 5'-H) |
| 7.28 | (dd, 1H, $J_{3',4'}$ = 7.7 Hz, $J_{3',5'}$ = 1.0 Hz, 3'-H) |
| 7.34 | (dd, 1H, $J_{4',6'}$ = 1.6 Hz, $J_{5',6'}$ = 7.7 Hz, 6'-H) |
| 8.49 | (s, ~1H, 1-H) |
| 9.24 | (bt, ~1H, 9'-NH) |

EXAMPLE 3

Assay for Amlodipine Maleate, Amlodipine Aspartate and Amlodipine Amide in Amlodipine Maleate Substance by HPLC 1. A Reference solution 1 was prepared by transferring approx. 32 mg of amlodipine maleate reference standard (having a known purity) into 50 ml volumetric flask and dissolving in a mixture of 0.02M acetate buffer pH 5.0 and acetonitrile (1:1 v/v).
2. The Reference solution 2 was prepared by transferring approx. 32 mg of amlodipine maleate mixed standard (a mixture of 4 weight parts of amlodipine maleate, 1 part of amlodipine aspartate and 1 part of amlodipine amide, each of high and generally known purity) into 50 ml volumetric flask and dissolving in a mixture of 0.02M acetate buffer pH 5.0 and acetonitrile (1:1 v/v)
3. A Sample solution was prepared by transferring approx. 32 mg of amlodipine maleate analysed sample into 50 ml volumetric flask and dissolving in a mixture of 0.02M acetate buffer pH 5.0 and acetonitrile (1:1 v/v)
4. Chromatographic procedure
a. Chromatographic conditions:

| Analytical column: | Symmetry C8 (Waters), 100 × 4.6 mm, $d_p$ = 3.5 μm |
|---|---|
| Guard column: | Sentry Guard column, Symmetry C8 (Waters), 20 × 3.9 mm, $d_p$ = 5 μm |
| Mobile phase: | A) 0.05M perchlorate buffer pH 2.75 and acetonitrile 65:35 (v/v) |
| | B) 0.05M perchlorate buffer pH 2.75 and acetonitrile 35:65 (v/v) |
| | Perchlorate buffer pH 2.75: Dissolve 7 g of NaClO$_4$.H$_2$O (0.05M) and 1.74 g K$_2$HPO$_4$ (0.01M) in 1,000 ml of water. Adjust to pH 2.75 by the addition of phosphoric acid. |
| Flow: | 1.0 ml/min, gradient |

-continued

| Gradient program: | Time (min) | % of A | % of B |
|---|---|---|---|
| | 0.0 | 100 | 0 |
| | 4.0 | 100 | 0 |
| | 14.0 | 35 | 65 |
| | 21.0 | 0 | 100 |
| | 28.0 | 0 | 100 |
| | 29.0 | 100 | 0 |
| | 32.0 | 100 | 0 |
| Detection: | UV, 237 nm | | |
| Column temperature: | 45° C. | | |
| Autosampler: | 4° C., light protected | | |

Injection volume: 10 μl
b. Injection procedure

After a stable baseline was obtained, the Reference solution 2 was injected and the resolution factor between amlodipine, aspartate and amide was calculated. The symmetry factor and number of theoretical plates were also calculated using general method of the European Pharmacopoeia for calculating system suitability parameters. The values obtained were as follows:

Resolution: amlo-aspartate/amlodipine=15.6, amlodipine/amlo-maleamide=20.1. Symmetry factor: amlodipine aspartate 1.2, amlodipine 1.3, amlodipine maleamide 1.2. No. of theoretical plates: amlodipine aspartate 6387, amlodipine 22 852, amlodipine maleamide 56676.

The Reference solution 1 and the Sample solution were then injected into the column.

5. Calculations:

The content of amlodipine maleate and content of the respective impurities in the analysed sample was calculated by comparing peak areas of the respective compounds in the sample solution chromatogram with corresponding peak areas obtained in chromatograms of reference solution 1 and 2 resp., taking into account the weighing and purity of reference samples and predetermined relative response factors (RRF). The RRF values and analysis limits for the individual impurities, as a percent of amlodipine, are listed in the following table:

| Compound | RRF | Analysis Limit (%) |
|---|---|---|
| Aspartate | 0.78 | 0.01 |
| Amide | 1.01 | 0.02 |

EXAMPLE 4

Assay for Amlodipine Maleate and Amlodipine Aspartate in Tablets Comprising Amlodipine Maleate in Amount Equivalent to 2.5 mg of Amlodipine Free Base by HPLC The assay is performed as described in Example 3 with the following changes:

Sample solution was prepared by transfering of 5 amlodipine tablets into a 25 ml volumetric flask. 20 ml of a mixture of 0.02M acetate buffer pH 5.0 and acetonitrile (1:1 v/v) was added and the mixture was swirled until all tablets were completely disintegrated. Subsequently, the mixture was placed in an ultrasonic bath for 5 minutes. The flask was filled with a mixture of 0.02M acetate buffer pH 5.0 and acetonitrile (1:1 v/v) up to volume and mixed. About 10 ml of obtained solution was centrifuged for 10 minutes at 4,000 rpm. The supernatant was used for analysis.

Essentially the same procedure may be used for analysis of tablets comprising 5 or 10 mg amlodipine maleate instead of 2.5 as above, with the proviso that 50 ml or 100 ml volumetric flasks are used respectively.

EXAMPLE 5

Figure 5:
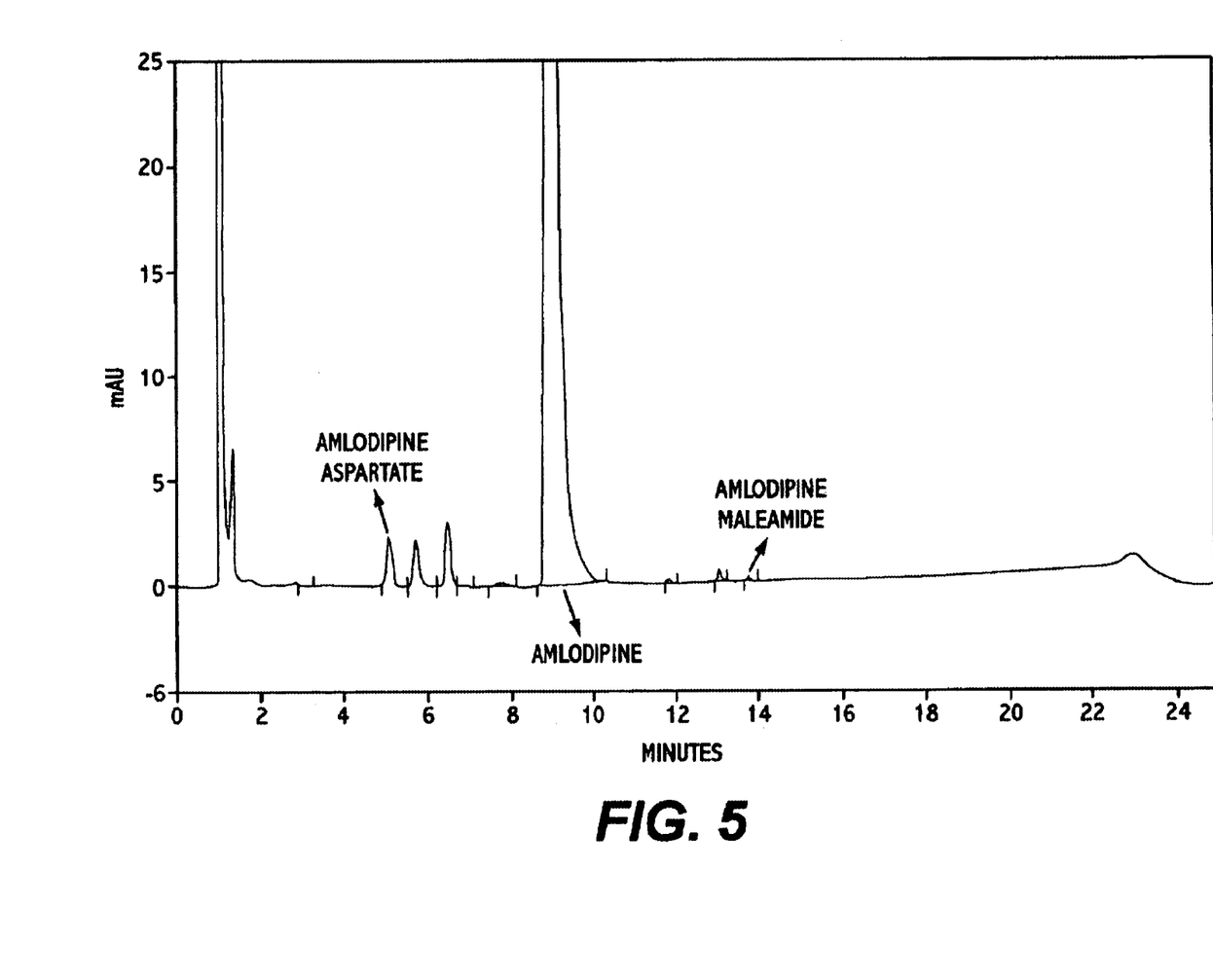
FIG. 5 shows an HPLC chromatogram of amlodipine maleate tablets having less than 0.2% amlodipine maleate or amlodipine aspartate.

From a lot of 10 mg amlodipine maleate tablets, a sample was taken and assayed for the presence of amlodipine aspartate and amlodipine maleamide via HPLC. The specification for these tablets to be deemed "acceptable" required that no more than 0.2% of either amlodipine aspartate or amlodipine maleamide be present therein. The HPLC chromatogram is shown in FIG. 5. The assay determined that the tablets contained 0.17% amlodipine aspartate and 0.01% amlodipine maleamide relative to the peak area of the amlodipine and thus the lot is acceptable/approved.
Comparison.

Figure 6:
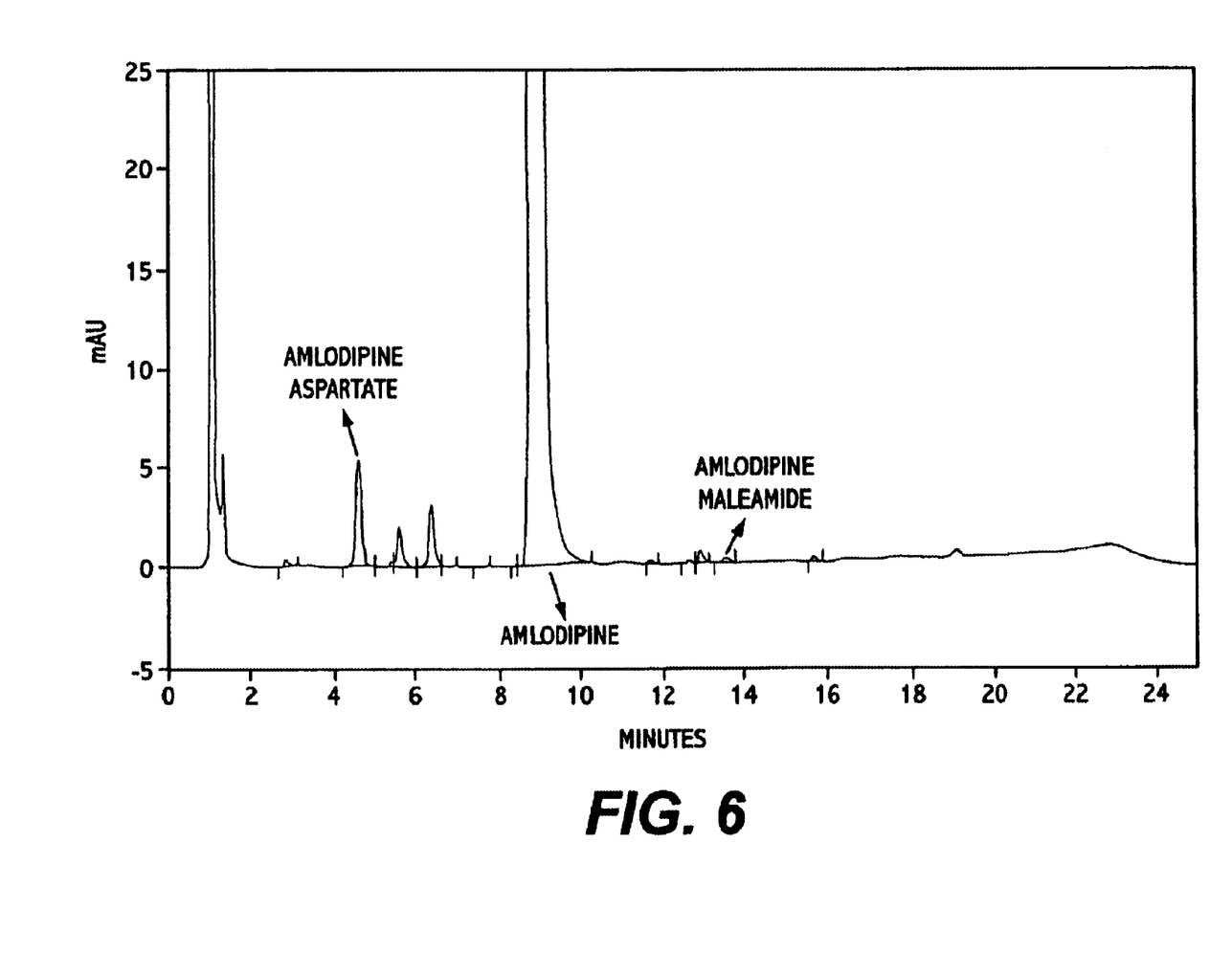
FIG. 6 shows an HPLC chromatogram of amlodipine maleate tablets having more than 0.2% amlodipine aspartate.

From a different lot of 10 mg amlodipine maleate tablets than as used above, a sample was taken and assayed for the presence of amlodipine aspartate and amlodipine maleamide via HPLC. The specification for these tablets to be deemed "acceptable" again required that no more than 0.2% of either amlodipine aspartate or amlodipine maleamide be present therein. The HPLC chromatogram is shown in FIG. 6. The assay determined that the tablets contained 0.42% amlodipine aspartate and 0.02% amlodipine maleamide relative to the peak area of the amlodipine and thus this lot is not acceptable and would not be approved or released.

EXAMPLE 6

Determination of Amlodipine Aspartate and Amlodipine Amide in Amlodipine Maleate Drug Substance by TLC 1. Description of the System Solvent: Water and methanol in the ratio of 50:50 (V/V).

Sample Solution A: Transfer about 51 mg of Amlodipine maleate raw material into a brown vial of 10 ml. Dissolve in 4 ml of solvent and homogenize the solution (equivalent to 10 mg Amlodipine per ml).

Amlo-Aspartate 0.3% Solution B: Transfer about 6 mg of Amlodipine aspartate into a volumetric flask of 25 ml. Add 20 ml of solvent and dissolve with the help of an ultrasonic bath. Make up to volume with solvent and homogenize the solution (stock solution B). Pipette 0.5 ml of stock solution B into a vial of 10 ml. Add 3.5 ml of solvent and homogenize the solution (equivalent to 0.03 mg Amlodipine per ml).

Amlo-Maleamide 0.3% Solution C: Transfer about 6 mg of Amlodipine maleamide into a volumetric flask of 25 ml. Add 20 ml of solvent and dissolve with the help of an ultrasonic bath. Make up to volume with solvent and homogenize the solution (stock solution C). Pipette 0.5 ml of stock solution C into a bottle. Add 3.5 ml of solvent and homogenize the solution (equivalent to 0.03 mg amlodipine per ml).

Mixed Standard D: Transfer about 51 mg of Amlodipine maleate raw material into a brown bottle. Dissolve in 3 ml of solvent. Add respectively 0.5 ml of stock solution B and 0.5 ml of stock solution C and homogenize the solution.

| Plate: | HPTLC plate covered with silicagel 60 F254, 20 × 10 cm (Merck) |
|---|---|
| Sample volume: | 1.0 μl. |

-continued

| | |
|---|---|
| Band: | 10 mm |
| Application speed: | 4 sec/μl |
| Distance from the lower margin HPTLC plate: | 15 mm. |
| Distance between samples: | 10 mm. |
| Mobile phase: | Methyl isobutyl keton, methanol and acetic acid in the ratio of 70:20:10 (V/V/V). |
| Saturation of the chamber: | Fill the conditioning tray with 20 ml mobile phase and saturate for 5 minutes |
| Development: | Separation path 9 cm, horizontal. |
| Air-drying: | 15 min, at ambient conditions. |
| Detection: | UV 366 nm. |

2. Evaluation of Chromatograms a. After all four solutions were placed on the plate, the TLC plate was dried in air and then viewed under UV-light at 366 nm. The test was not valid unless the chromatogram obtained with the Mixed standard D exhibited three clearly separated spots.

b. The intensity of any secondary spot on the solution A chromatogram corresponding in Rf value to the main spot obtained with solution B (equivalent to 0.3% of the aspartate) was estimated.

c. The intensity of any secondary spot on the solution A chromatogram corresponding in Rf value to the main spot obtained with standard solution C (equivalent to 0.3% of the amide) was estimated.

3. Results

Figure 7:
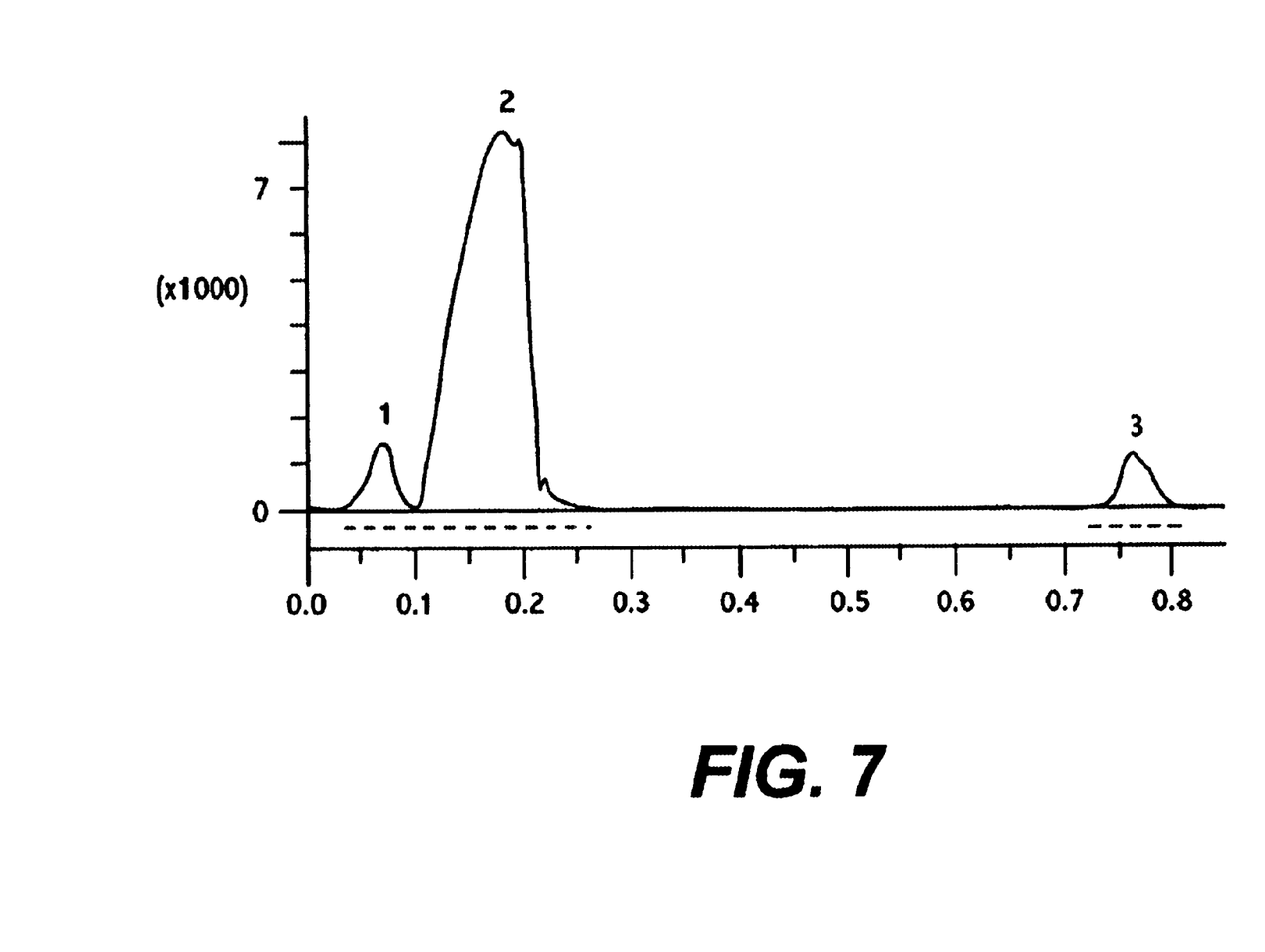
FIG. 7 shows a scanned TLC chromatogram of amlodipine maleate impurified with amlodipine aspartate and amlodipine maleamide.

An example of a chromatogram of the mixture of amlodipine maleate, amlodipine aspartate and amlodipine maleamide, vizualized by scanning on a Camag video scan system, is shown in FIG. 7.

| Substance | Rf |
|---|---|
| Amlodipine aspartate | 0.06 |
| Amlodipine maleate | 0.19 |
| Amlodipine maleamide | 0.76 |

The invention having been described, it will be readily apparent to those skilled in the art that further changes and modifications in actual implementation of the concepts and embodiments described herein can easily be made or may be learned by practice of the invention, without departing from the spirit and scope of the invention as defined by the following claims.

We claim:

1. A process, which comprises assaying a substantially pure amlodipine aspartate or amlodipine maleamide under a set of conditions to obtain a reference standard analytical result for said set of conditions.

2. The process according to claim 1, wherein said assay is thin layer chromatography and said conditions include a solvent, the concentration of amlodipine aspartate or amlodipine maleamide in said solvent, and amount of amlodipine aspartate or amlodipine maleamide applied to and wherein said reference standard analytical result is the $R_f$ value and/or the size of a spot produced on a chromatogram corresponding to said amlodipine aspartate or amlodipine maleamide.

3. The process according to claim 1, wherein said assay is high performance liquid chromatography (HPLC) and said conditions include a solvent, the concentration of amlodipine aspartate or amlodipine maleamide in said solvent, and the amount amlodipine aspartate or amlodipine maleamide applied to a chromatographic column and wherein said reference standard analytical result is a resolution factor or retention time, peak area and/or a response factor of a peak corresponding to said amlodipine aspartate or amlodipine maleamide on a chromatogram.

4. A process of testing purity or stability of a sample of amlodipine maleate or a pharmaceutical dosage form comprising amlodipine maleate which comprises assaying a sample of an amlodipine maleate substance or composition for the presence of amlodipine aspartate or amlodipine maleamide.

5. The process according to claim 4, which comprises:

assaying an amlodipine maleate substance or composition to obtain an analytical result; and comparing said analytical result to a corresponding reference standard analytical result for amlodipine aspartate or amlodipine maleamide to determine if the purity or stability of said amlodipine maleate substance or composition is satisfactory.

6. The process according to claim 4, wherein said purity or stability is satisfactory if the amount of amlodipine aspartate or amlodipine maleamide relative to amlodipine maleate is determined to be less than 0.2 wt %.

7. A process for determining the presence of an impurity in a sample containing amlodipine maleate which comprises the steps of:

a) dissolving a sample comprising amlodipine maleate in a solvent to produce a sample solution;

b) dissolving a sample of amlodipine aspartate or amlodipine maleamide in a solvent to produce a reference solution;

c) subjecting the sample solution and the reference solution to thin layer chromatography (TLC) to obtain a chromatogram for each; and d) estimating the intensity of any secondary spot obtained from the sample solution which corresponds in $R_f$ value to amlodipine aspartate or amlodipine maleamide, against the intensity of the spot due to the aspartate or maleamide in the chromatograph of the reference solution.

8. A process for determining the presence of an impurity which comprises the steps of:

a) dissolving a sample comprising amlodipine maleate in a solvent to produce one or more sample solutions;

b) dissolving a sample of amlodipine aspartate or amlodipine maleamide in a solvent to produce a reference solution;

c) injecting the sample and reference solutions into an high performance liquid chromatography (HPLC) column; and d) estimating the peak areas of each sample and reference solution on a chromatogram and calculating from these the content of the amlodipine aspartate or the amlodipine maleamide in each sample solution.

9. A process which comprises separating amlodipine maleate from either amlodipine aspartate or amlodipine maleamide.

10. The process according to claim 9, wherein said separation is carried out by thin layer chromatography.

11. The process according to claim 9, herein said separation is carried out by high performance liquid chromatography (HPLC).

12. A process, which comprises blending amlodipine maleate with at least one pharmaceutically acceptable excipient to form a blend;

either (a) filling said blend into capsules or (2) compressing said blend in to tablets, to form a production lot of amlodipine maleate pharmaceutical solid dosage forms;

removing a sample of said amlodipine maleate pharmaceutical solid dosage forms from said production lot;

subjecting said sample to an assay to obtain a sample analytical result;

comparing said sample analytical result to a corresponding reference standard analytical result for amlodipine aspartate or amlodipine maleamide to determine the amount of amlodipine aspartate or amlodipine maleamide relative to said amlodipine maleate in said sample; and selling or releasing said production lot if the amount of amlodipine aspartate or amlodipine maleamide in said sample is not greater than 1.0 wt % based on the amount of amlodipine maleate.

13. The process according to claim 12, wherein said reference standard analytical result was determined prior to said blending step.

14. The process according to claim 13, wherein said comparing step uses an electronically stored representation of said reference standard analytical result.

15. The process according to claim 12, wherein said comparing step comprises a visual inspection of said sample analytical result and said reference standard analytical result.

16. The process according to claim 12, wherein said production lot released or sold if the amount of amlodipine aspartate or amlodipine maleamide in said sample is not greater than 0.2 wt % based on the amount of amlodipine maleate.

* * * * *